United States Patent
Stender et al.

(10) Patent No.: US 8,173,785 B2
(45) Date of Patent: May 8, 2012

(54) **PEPTIDE NUCLEIC ACID PROBES FOR ANALYSIS OF CERTAIN *STAPHYLOCOCCUS* SPECIES**

(75) Inventors: Henrik Stender, Gentofte (DK); Mark Fiandaca, Princeton, MA (US); Kenneth Oliveira, Boston, MA (US); Elizabeth Bergeron, Londonderry, NH (US)

(73) Assignee: AdvanDx, Inc., Woburn, MA (US)

( * ) Notice: Subject to any disclaimer, the term of this patent is extended or adjusted under 35 U.S.C. 154(b) by 601 days.

(21) Appl. No.: 10/580,727

(22) PCT Filed: Nov. 24, 2004

(86) PCT No.: PCT/US2004/039781
§ 371 (c)(1), (2), (4) Date: Jul. 3, 2007

(87) PCT Pub. No.: WO2005/054516
PCT Pub. Date: Jun. 16, 2005

(65) Prior Publication Data
US 2008/0008994 A1   Jan. 10, 2008

Related U.S. Application Data

(60) Provisional application No. 60/525,591, filed on Nov. 26, 2003.

(51) Int. Cl.
*C07H 19/00* (2006.01)

(52) U.S. Cl. .................... 536/22.1; 536/24.32
(58) Field of Classification Search .................. None
See application file for complete search history.

(56) References Cited

U.S. PATENT DOCUMENTS

| | | | |
|---|---|---|---|
| 6,380,370 | B1 | 4/2002 | Doucette-Stamm et al. |
| 2006/0140972 | A1 | 6/2006 | Alm et al. |

FOREIGN PATENT DOCUMENTS

| | | |
|---|---|---|
| EP | 1096024 A1 | 5/2001 |
| WO | 96/00298 A1 | 1/1996 |
| WO | 99/01572 A2 | 1/1999 |
| WO | 9954502 A1 | 10/1999 |
| WO | 00/66788 A2 | 11/2000 |
| WO | 01/31055 A2 | 5/2001 |
| WO | 03/052128 A1 | 6/2003 |
| WO | 03/106676 | * 12/2003 |
| WO | 2005/054516 A2 | 6/2005 |
| WO | 2005054516 A2 | 6/2005 |

OTHER PUBLICATIONS

Ray et al (FASEB Journal, 14:1041-1060, 2000).*
Krimmer V. et al. "Detection of *Staphylococcus aureus* and *Staphylococcus epidermidis* in clinical samples by 16S rRNA-directed in situ hybridization." J. Clin Microbiol Aug. 1999;37(8):2667-73.

* cited by examiner

*Primary Examiner* — Patricia A Duffy
(74) *Attorney, Agent, or Firm* — McCarter & English, LLP; Jonathan M. Sparks

(57) ABSTRACT

The present invention relates to peptide nucleic acid (PNA) probes, PNA probe sets and methods for the analysis of certain *Staphylococcus* species optionally present in a sample. The invention further relates to diagnostic kits comprising such PNA probes or PNA probe sets.

6 Claims, No Drawings

SEQUENCE LISTING

```
<160> NUMBER OF SEQ ID NOS: 12

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tctaacatgt tcttt                                                          15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tctagtctgt tcttt                                                          15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tctaatatat tcctt                                                          15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tctaatatat acttt                                                          15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gctccaaatg gttac                                                          15
```

```
<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tcctcgtctg ttcgc                                                    15

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ctccttatct gttcgc                                                   16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
ctccttgtct gttcgc                                                   16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
cttctcatct gttcgc                                                   16

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tcctcgtccg ttcgc                                                    15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tccttgtccg ttcgc                                                    15

<210> SEQ ID NO 12
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gcttctcgtc cgttc                                                      15
```

US 8,173,785 B2

PEPTIDE NUCLEIC ACID PROBES FOR ANALYSIS OF CERTAIN *STAPHYLOCOCCUS* SPECIES

RELATED APPLICATIONS

This application claims the benefit of U.S. Provisional Ser. No. 60/525,591, filed Nov. 26, 2003 and PCT Applcation No. PCT/US2004/039781, filed Nov. 24, 2004. The entire contents of which are incorporated herein by reference in their entirety.

FIELD OF THE INVENTION

The present invention relates to peptide nucleic acid (PNA) probes, PNA probe sets and methods for the analysis of certain *Staphylococcus* species optionally present in a sample. The invention further relates to diagnostic kits comprising such PNA probes or PNA probe sets. The methods and kits of the invention are particularly useful for simultaneous analysis of one or more of *Staphylococcus* species other than *S. aureus* and of *S. aureus*.

BACKGROUND

*Staphylococcus aureus* is a well-known human pathogen associated with surgical site infections, bloodstream infections (BSI) and other serious infections. In contrast, other *Staphylococcus* species, such as particularly *Staphylococcus epidermidis, Staphylococcus haemolyticus, Staphylococcus hominis, Staphylococcus lugdenensis*, and *Staphylococcus saprophyticus* commonly found on the skin, are with the exception of catheter-related infections rarely of clinical significance. Furthermore, in those instances where a BSI is caused by a *Staphylococcus* species other than *S. aureus* there is often a difference in antibiotic susceptibility or viability between those organisms and S. aureus. Differentiation between *Staphylococcus* species other than *S. aureus* and *S. aureus* is therefore extremely important for directing appropriate patient therapy and patient management.

The presence of *Staphylococcus* species in clinical specimens is routinely determined by the presence of Gram-positive cocci in clusters (GPCC) by Gram staining and microscopic analysis, however; differentiation between *S. aureus* and other *Staphylococcus* species must await subculture, overnight incubation followed by biochemical analysis, such as coagulase and latex agglutination testing, or more recently by molecular testing. The presence of other *Staphylococcus* species is often determined on the basis of a negative tube coagulase test result and is typically reported as coagulase-negative staphylococci (CNS). This is particularly problematic for analysis of GPCC positive blood culture bottles as only 20-30% of GPCC positive blood bottles are due to *S. aureus* (Karlowsky et al., *Ann Clin Microbiol Antimicrob* 3:7 (2004)). In the majority of cases physicians therefore have to make decisions based on negative test results, e.g., absence of *S. aureus*.

DNA probes for analysis of *Staphylococcus aureus* and all *Staphylococcus* species (genus-specific probes) have been described (WO0066788, Kempf et al., *J. Clin. Microbiol* 38:830-838 (2000)) as well as PNA probes for the analysis of *S. aureus* (U.S. Pat. No. 6,664,045, Oliveira et al., J. Clin. Microbiol. 40:247-251 (2002)). These probes all target sequences that are either species-specific or genus-specific.

Comparative analysis of ribosomal RNA (rRNA) sequences or genomic DNA sequences corresponding to said rRNA (rDNA) has become a widely accepted method for establishing phylogenetic relationships between bacterial species (Woese, *Microbiol. Rev.* 51:221-271 (1987)). Consequently, Bergey's Manual of systematic bacteriology has been revised based on rRNA or rDNA sequence comparisons. Ribosomal RNA or rDNA sequence differences between closely related species enable design of species-specific probes for microbial identification thus enabling diagnostic microbiology to be based on a single genetic marker rather than a series of phenotypic markers as in traditional microbiology (Delong et al., *Science* 342:1360-1363 (1989)). However, the design of probes targeting a cohort of species is particularly problematic and requires a combination of highly specific probe constructs and unique target sequences.

PNAs are useful candidates for investigation when developing probes targeting a subset of species because they hybridize to nucleic acids with increased sequence specificity as compared to DNA probes. Prior art therefore also comprises examples of PNA probes targeting mycobacteria other than *Mycobacterium tuberculosis* (U.S. Pat. No. 6,753,421) and enterococci other than *Enterococcus faecalis* (Oliveira et al., Abstract #D-2003, Interscience Conference on Antimicrobial Agents and Chemotherapy, Sept. 27-30, 2002, San Diego, Calif.).

Despite its name, Peptide Nucleic Acid (PNA) is neither a peptide nor a nucleic acid, it is not even an acid. PNA is a non-naturally occurring polyamide that can hybridize to nucleic acids (DNA and RNA) with sequence specificity according to Watson-Crick base paring rules (See: U.S. Pat. No. 5,539,082) and Egholm et al., *Nature* 365:566-568 (1993)). However, whereas nucleic acids are biological materials that play a central role in the life of living species as agents of genetic transmission and expression, PNA is a recently developed totally artificial molecule, conceived in the minds of chemists and made using synthetic organic chemistry. PNA also differs structurally from nucleic acid. Although both can employ common nucleobases (A, C, G, T, and U), the backbones of these molecules are structurally diverse. The backbones of RNA and DNA are composed of repeating phosphodiester ribose and 2-deoxyribose units. In contrast, the backbones of the most common PNAs are composed on (aminoethyl)-glycine subunits. Additionally, in PNA the nucleobases are connected to the backbone by an additional methylene carbonyl moiety. PNA is therefore not an acid and therefore contains no charged acidic groups such as those present in DNA and RNA. The non-charged backbone allows PNA probes to hybridize under conditions that are destabilizing to DNA and RNA. Such attributes enable PNA probes to access targets, such as highly structured rRNA and double stranded DNA, known to be inaccessible to DNA probes (See: Stephano & Hyidig-Nielsen, IBC Library Series Publication #948. International Business Communication, Southborough, Mass., pp. 19-37 (1997)). PNA probes are not the equivalent of nucleic acid probes in structure or function.

Positive identification of *Staphylococcus* species other than *S. aureus* would be advantageous in many cases and simultaneous analysis of both *S. aureus* and other *Staphylococcus* species would be ideal as treatment decisions for the presence of either *S. aureus* or other *Staphylococcus* species would always be based on a positive test results. This feature would also offer a significant advantage when a mixture of *S. aureus* and other *Staphylococcus* species are present.

SUMMARY OF THE INVENTION

This invention is directed to PNA probes, or PNA probe sets and their use as well as kits useful for the analysis of certain *Staphylococcus* species, preferably those other than

*Staphylococcus aureus* optionally present in a sample of interest. In accordance with the claims, the PNA probes are directed to ribosomal RNA (rRNA) or the genomic sequences corresponding to said rRNA (rDNA) or its complement.

In one embodiment, this invention is directed to PNA probes for analysis of one *Staphylococcus* species other than *S. aureus*, such as but not limited to *Staphylococcus epidermidis, Staphylococcus haemolyticus, Staphylococcus hominis, Staphylococcus lugdenensis,* and *Staphylococcus saprophyticus*.

In another embodiment, this invention is directed to PNA probes for analysis of two or more *Staphylococcus* species other than *S. aureus*.

PNA probes (originally described in U.S. Pat. No. 5,539,082 and Egholm et al., Nature 365:566-568 (1993), herein attached as reference) have inherent physico/chemical characteristics as compared to naturally occurring nucleic acid probes, which allow the design of rapid and accurate assays. PNA probes offer another advantage over nucleic acid probes when applied in fluorescence in situ hybridization (FISH) assays due to their improved cellular penetration of the rigid cell wall of Gram-positive bacteria such as *Staphylococcus* species. Where nucleic acid probes require fixation and permeabilization with cross-linking agents and/or enzymes (for example see Kempf et al., i J. Clin. Microbiol 38:830-838 (2000)), PNA probes can be applied directly following smear preparation as exemplified in Example 1.

In preferred embodiments, PNA probes have relatively short nucleobase sequences, such as 15 nucleobases as described in Example 1. Naturally occurring nucleic acid probes due to their weaker stabilities and lower melting temperatures (Tm) are typically at least 18 nucleobases in length (For example see Kempf et al., *J. Clin. Microbiol* 38:830-838 (2000)). The greater specificity of PNA probes provides better discrimination to closely related non-target sequences with a single or just a few nucleobase difference(s) as required for analysis of rRNA or rDNA of closely related *Staphylococcus* species.

Exemplary PNA probe nucleobase sequences according to the invention include: TCT-AAC-ATG-TTC-TTT (Seq. Id. No. 1) targeting *Staphylococcus epidermidis*, TCT-AGT-CTG-TTC-TTT (Seq. Id. No. 2) targeting *Staphylococcus saprophyticus*, TCT-AAT-ATA-TTC-CTT (Seq. Id. No. 3) targeting *Staphylococcus haemolyticus*, TCT-AAT-ATA-TAC-TTT (Seq. Id. No. 4) targeting *Staphylococcus warneri*, GCT-CCA-AAT-GGT-TAC (Seq. Id. No. 5) targeting several *Staphylococcus* species other than *Staphylococcus aureus*, TCC-TCG-TCT-GTT-CGC (Seq. Id. No. 6) targeting *Staphylococcus epidermidis*, CTC-CTT-ATC-TGT-TCG-C (Seq. Id. No. 7) targeting *Staphylococcus saprophyticus*, CTC-CTT-GTC-TGT-TCG-C (Seq. Id. No. 8) targeting *Staphylococcus haemolyticus*, CTT-CTC-ATC-TGT-TCG-C (Seq. Id. No. 9), targeting *Staphylococcus sciuri*, TCC-TCG-TCC-GTT-CGC (Seq. Id. No. 10), targeting *Staphylococcus schleiferi*, and TCC-TTG-TCC-GTT-CGC (Seq. Id. No. 11) targeting a variant of *Staphylococcus schleiferi*. Though these PNA probes are described by the species of *staphylococci* they are targeted against, they are not necessarily specific for that particular organism, and, in fact, several of the probes are perfectly complementary, or nearly perfectly complementary to targets in other *Staphylococcus* species.

In yet another embodiment, the PNA probes may be part of a PNA probe set comprising either two or more PNA probes for analysis of two or more species of *Staphylococcus* species other than *S. aureus* or at least one PNA probe for analysis of *Staphylococcus* species other than *S. aureus* and a PNA probe for analysis of *S. aureus*. That is, some PNA probes of the invention are specific for two or more species of *Staphylococcus* species other then *S. aureus*. Preferably, PNA probes within a PNA probe set are differently labeled for independent analysis of two or more *Staphylococcus* species. In a modification of this embodiment, and as exemplified in Example 5, multiple probes may be identically labeled to detect a particular *Staphylococcus* species or cohort of *Staphylococcus* species, while an optional other probe or probes is differently labeled for analysis of a second species or cohort of species.

The method according to the invention comprises contacting a sample with one or more of the PNA probes described above. According to the method, the presence, absence and/or number of *Staphylococcus* species other than *Staphylococcus aureus* are detected, identified and/or quantitated by correlating the hybridization, under suitable hybridization conditions, of the probing nucleobase sequence of the probe to the target sequence. Consequently, the analysis is based on a single assay with a definitive outcome. In contrast, current routine methods for definitive analysis of *Staphylococcus* species other than *S. aureus* are based on multiple phenotypic characteristics involving multiple tests.

In another embodiment, the PNA probes are applied simultaneously with previously published PNA probes for analysis of *Staphylococcus aureus* (see Oliveira et al., J. Clin. Microbiol. 40:247-251 (2002)) either in parallel reactions or in the same reaction (multiplex) for simultaneous analysis of *Staphylococcus aureus* and *Staphylococcus* species other than *S. aureus*. This way the presence of *Staphylococcus* species other than *S. aureus* are further supported by the absence of *S. aureus* specific signal or visa versa, such final test results are interpreted on the basis on both a positive and a negative reaction. The PNA probe set therefore provides internal controls which eliminate the need to perform separate control experiments. Preferably, the two PNA probes are independently labeled such that the analysis is performed in one reaction (multiplex). Simultaneous analysis is also an advantage for specimens containing a mixture of both *S. aureus* and *Staphylococcus* species other than *S. aureus*. In such cases the use of the PNA probes for FISH offers the advantage of single cell detection, such that cells of both *Staphylococcus* species other than 1, and *S. aureus* can be viewed simultaneously and differentiated by specific labels as exemplified below. In contrast other technologies are not able to distinguish mixed cultures from false-positive reactions without performing additional control experiments.

In still another embodiment, this invention is directed to kits suitable for performing an assay that detects, identifies and/or quantitates *Staphylococcus* species other than *Staphylococcus aureus* optionally present in a sample and/or determination of antibiotic resistance. The kits of this invention comprise one or more PNA probes and other reagents or compositions that are selected to perform an assay or otherwise simplify the performance of an assay. In particular, the combined analysis of *Staphylococcus* species other than *S. aureus* and *Staphylococcus aureus* is well-suited for routine testing of GPCC positive blood culture bottles where the use of multiple PNA probes serve secondarily as internal controls.

Another benefit derived from the use of multiple PNA probes is the use of blocking probes. In this preferred embodiment, the blocking probe strategy is employed in the design of probes for use in a multiplex assay where probes are directed against similar regions of conserved target molecules in closely related organisms. For example, a pair of independently detectable probes which are substantially similar in nucleobase sequence and Tm may be designed to hybridize to highly conserved regions of two targets in which the targeted nucleobase sequences differ by only one base. In this case, the tendency of the first probe to hybridize non-specifically to the complementary target of the second probe is discouraged by the presence and relative stability of the second probe/target hybrid. Similarly, multiple probes may be designed which are either independently detectable or non-independently detectable, or a combination of independently and non-independently detectable, which all differ from one another by as little as a single base, and which are complementary, or at least substantially complementary to partially conserved target regions of phylogenetically related organisms. The competition for target sites can result in higher probe specificities, while lowering the likelihood of cross hybridization.

Those of ordinary skill in the art will appreciate that a suitable PNA probe need not have exactly these probing nucleobase sequences described herein to be operative but may be modified according to the particular assay conditions. For example, shorter PNA probes can be prepared by truncation of the nucleobase sequence if the stability of the hybrid needs to be modified to thereby lower the Tm and/or adjust for stringency. Similarly, the nucleobase sequence may be truncated at one end and extended at the other end as long as the discriminating nucleobases remain within the sequence of the PNA probe. Such variations of the probing nucleobase sequences within the parameters described herein are considered to be embodiments of this invention.

Those of ordinary skill in the art will also appreciate that the complement probing sequence is equally suitable for assays, such as but not limited to real-time PCR, that are directed against rDNA as a target sequence.

DETAILED DESCRIPTION OF THE INVENTION

1. Definitions:

As used herein, the term "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids.

As used herein, the term "nucleobase sequence" means any segment of a polymer that comprises nucleobase-containing subunits. Non-limiting examples of suitable polymers or polymer segments include oligodeoxynucleotides, oligoribonucleotides, peptide nucleic acids, nucleic acid analogs, nucleic acid mimics, and/or chimeras.

As used herein, the term "target sequence" means the nucleobase sequence that is to be detected in an assay.

As used herein, the term "probe" means a polymer (e. g. a DNA, RNA, PNA, chimera or linked polymer) having a probing nucleobase sequence that is designed to sequence-specifically hybridize to a target sequence of a target molecule of an organism of interest.

As used herein, the term "peptide nucleic acid" or "PNA" means any oligomer, linked polymer or chimeric oligomer, comprising two or more PNA subunits (residues), including any of the polymers referred to or claimed as peptide nucleic acids in U.S. Pat. Nos. 5,539,082, 5,527,675, 5,623,049, 5,714,331, 5,736,336, 5,773,571, 5,786,461, 5,837,459, 5,891,625, 5,972,610, 5,986,053, 6,107,470 and 6,357,163. In the most preferred embodiment, a PNA subunit consists of a naturally occurring or non-naturally occurring nucleobase attached to the aza nitrogen of the N-[2-(aminoethyl)] glycine backbone through a methylene carbonyl linkage.

As used herein, the terms "label" and "detectable moiety" are interchangeable and shall refer to moieties that can be attached to a probe to thereby render the probe detectable by an instrument or method.

Reference herein to "*Staphylococcus* species other than *S. aureus*," or a related phrase means essentially one or more *Staphylococcus* species of the *Staphylococcus* genus except for *S. aureus*. With a few exceptions, *Staphylococcus* species other than *S. aureus* is equivalent to coagulase-negative staphylococci, which is a medical expression for *Staphylococcus* species other than *S. aureus*. A cohort of *Staphylococcus* species other than *S. aureus* essentially means two of more species of *Staphylococcus* species other than *S. aureus* and may comprise all coagulase-negative staphylococci, clinically significant coagulase-negative staphylococci or a subset of these. *Staphylococcus* species other than *Staphylococcus aureus*, may include, for example *S. capitis, S.cohnii, S. epidermidis, S. saprophyticus, S. intermedius, S. hyicus, S. haemolyticus, S. hominis, S. Iugdunensis, S. saccharolyticus, S. schleiferi, S. sciuri, S. simulans, S. warneri* and/or *S. xylosus*.

The term "sample" as used herein refers to any biological sample or clinical sample that could contain an analyte for detection. Preferably the biological sample is in liquid form or as a tissue sample. Most preferably, the sample is from blood culture. Liquid samples include clinical samples, e.g. urine, blood, wounds, sputum, laryngeal swabs, gastric lavage, bronchial washings, aspirates, serum, nasal discharge, sweat, plasma, semen, cerebrospinal fluid, tears, pus, amniotic fluid, saliva, lung aspirate, gastrointestinal contents, vaginal discharge, urethral discharge, expectorates and cultures thereof. Preferred tissue samples or cultures thereof include chorionic villi specimens, skin epithelials, genitalia epithelials, gum epithelials, throat epithelials, hair and biopsies. Tissue samples may be either freshly prepared, or preserved for some time in a fixative such as but not limited to ethanol, methanol, paraformaldehyde, glutaraldehyde, formalin, paraffin, formaldehyde, formamide, or mixtures thereof. Non-clinical samples include food, beverages, water, pharmaceutical products, personal care products, dairy products or environmental samples and cultures thereof.

As used herein, "multiplex assay" includes assays in which multiple targets can potentially be detected, and identified. Identification can be specific, e.g., a particular species of microorganism, or generic, e.g., a particular genus of microorganism. Generic identification may also include the identification of a cohort of species of microorganisms, which includes one or more members of a defined group of species. One example of a defined group of species is the coagulase-negative staphylococci.

As used herein, independent and simultaneous detection includes an assay that can at once yield identification results for more than one target. For example, the detection of one or species of *Staphylococcus* other than aureus, and *Staphylococcus aureus* may be done at the same time with unique labels for each probe, thus resulting in independent and simultaneous detection.

Other reagents or compositions necessary to perform the assay, may include, for example, wash solutions, slides, coverslips, one or more PNA probes according to the invention, culture vessels, slide warmer, incubator, mounting fluid, and PCR components, including enzymes and buffers.

2. Description

I. General:

PNA Synthesis:

Methods for the chemical assembly of PNAs are well known (see: U.S. Pat. Nos. 5,539,082, 5,527,675, 5,623,049, 5,714,331, 5,736,336, 5,773,571, 5,786,461, 5,837,459, 5,891,625, 5,972,610, 5,986,053 and 6,107,470).

PNA Labeling:

Preferred non-limiting methods for labeling PNAs are described in U.S. Pat. Nos. 6,110,676, 6,361,942, and 6,355, 421, the examples section of these specifications or are otherwise well known in the art of PNA synthesis and peptide synthesis.

Labels:

Non-limiting examples of detectable moieties (labels) suitable for labeling PNA probes used in the practice of this invention would include a dextran conjugate, a branched nucleic acid detection system, a chromophore, a fluorophore, a spin label, a radioisotope, an enzyme, a hapten, an acridinium ester and a chemiluminescent compound.

Other suitable labeling reagents and preferred methods of attachment would be recognized by those of ordinary skill in the art of PNA, peptide or nucleic acid synthesis.

Preferred haptens include 5 (6)-carboxyfluorescein, 2,4-dinitrophenyl, digoxigenin, and biotin.

Preferred fluorochromes (fluorophores) include 5 (6)-carboxyfluorescein (Flu), tetramethyl-6-carboxyrhodamine (tamra), 6-((7-amino-4-methylcoumarin-3-acetyl) amino) hexanoic acid (Cou), 5 (and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), JOE, Tamara or the Alexa dye series (Molecular Probes, Eugene, Oreg.).

Preferred enzymes include polymerases (e. g. Taq polymerase, Klenow PNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP).

Unlabeled Probes:

The probes that are used for the practice of this invention need not be labeled with a detectable moiety to be operable within the methods of this invention, for example, the probes of the invention may be attached to a solid support, which renders them detectable by known array technologies.

Self-Indicating Probes:

Beacon probes are examples of self-indicating probes which include a donor moiety and an acceptor moiety. The donor and acceptor moieties operate such that the acceptor moieties accept energy transferred from the donor moieties or otherwise quench signal from the donor moiety. Though the previously listed fluorophores (with suitable spectral properties) might also operate as energy transfer acceptors, preferably, the acceptor moiety is a quencher moiety. Preferably, the quencher moiety is a non-fluorescent aromatic or heteroaromatic moiety. The preferred quencher moiety is 4-((-4-(dimethylamino) phenyl) azo) benzoic acid (dabcyl). In a preferred embodiment, the self-indicating Beacon probe is a PNA Linear Beacon as more fully described in U.S. Pat. No. 6,485,901.

In another embodiment, the self-indicating probes of this invention are of the type described in WIPO patent application WO97/45539. These self-indicating probes differ as compared with Beacon probes primarily in that the reporter must interact with the nucleic acid to produce signal.

Spacer/Linker Moieties:

Generally, spacers are used to minimize the adverse effects that bulky labeling reagents might have on hybridization properties of probes. Preferred spacer/linker moieties for the nucleobase polymers of this invention consist of one or more aminoalkyl carboxylic acids (e.g.,aminocaproic acid), the side chain of an amino acid (e.g., the side chain of lysine or ornithine), natural amino acids (e.g., glycine), aminooxyalkylacids (e.g., 8-amino-3,6-dioxaoctanoic acid), alkyl diacids (e.g., succinic acid), alkyloxy diacids (e.g., diglycolic acid) or alkyldiamines (e.g., 1,8-diamino-3,6-dioxaoctane).

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (e.g., ionic strength), hybridization temperature, detergent concentration, pH and the presence or absence of chaotropes. Stringency for a probe/target sequence combination is often found by the well-known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Stringency for an assay may be experimentally determined by examination of each stringency factor until the desired degree of discrimination is achieved.

Suitable Hybridization Conditions:

Generally, the more closely related the background causing nucleic acid contaminants are to the target sequence, the more carefully stringency must be controlled. Blocking probes may also be used as a means to improve discrimination beyond the limits possible by optimization of stringency factors. Suitable hybridization conditions will thus comprise conditions under which the desired degree of discrimination is achieved such that an assay generates an accurate (within the tolerance desired for the assay) and reproducible result.

Aided by no more than routine experimentation and the disclosure provided herein, those of skill in the art will easily be able to determine suitable hybridization conditions for performing assays utilizing the methods and compositions described herein. Suitable in situ hybridization or PCR conditions comprise conditions suitable for performing an in situ hybridization or PCR procedure. Thus, suitable in situ hybridization or PCR conditions will become apparent to those of skill in the art using the disclosure provided herein, with or without additional routine experimentation.

Blocking Probes:

Blocking probes are nucleic acid or non-nucleic acid probes that can be used to suppress the binding of the probing nucleobase sequence of the probing polymer to a non-target sequence. Preferred blocking probes are PNA probes (see: U.S. Pat. No. 6,110,676). It is believed that blocking probes operate by hybridization to the non-target sequence to thereby form a more thermodynamically stable complex than is formed by hybridization between the probing nucleobase sequence and the non-target sequence. Through formation of the more stable and preferred complex, the less stable non-preferred complex between the probing nucleobase sequence and the non-target sequence is prevented from forming. Thus, blocking probes can be used with the methods, kits and compositions of this invention to suppress the binding of the probes to a non-target sequence that might be present and interfere with the performance of the assay.

Probing Nucleobase Sequence:

The probing nucleobase sequence of a probe of this invention is the specific sequence recognition portion of the construct. Therefore, the probing nucleobase sequence is a nucleobase sequence designed to hybridize to a specific target sequence wherein the presence, absence or amount of the target sequence can be used to directly or indirectly detect the presence, absence or number of organisms of interest in a sample. Consequently, with due consideration to the requirements of a probe for the assay format chosen, the length and sequence composition of the probing nucleobase sequence of the probe will generally be chosen such that a stable complex is formed with the target sequence under suitable hybridization conditions.

The preferred nucleobase sequences of the probes of this invention for analysis of Staphylococcus species other than *S. aureus* are: TCT-AAC-ATG-TTC-TTT (Seq. ID. No. 1), TCT-AGT-CTG-TTC-TTT (Seq. ID. No. 2), TCT-AAT-ATA-TTC-CTT (Seq. ID. No. 3), TCT-AAT-ATA-TAC-TTT (Seq. ID. No. 4), GCT-CCA-AAT-GGT-TAC (Seq. ID. No. 5), TCC-TCG-TCT-GTT-CGC (Seq. Id. No. 6), CTC-CTT-ATC-TGT-TCG-C (Seq. Id. No. 7), CTC-CTT-GTC-TGT-TCG-C (Seq. Id. No. 8), CTT-CTC-ATC-TGT-TCG-C (Seq. Id. No. 9), TCC-TCG-TCC-GTT-CGC (Seq. Id. No. 10), TCC-TTG-TCC-GTT-CGC (Seq. Id. No. 11) and the complements thereof.

This invention contemplates that variation in these identified probing nucleobase sequences shall also provide probes that are suitable for the analysis of *Staphylococcus* species other than *S. aureus*. Such variation of the probing nucleobase sequences within the parameters described herein are considered to be an embodiment of this invention. Common variations include, deletions, insertions and frame shifts. Additionally, a shorter probing nucleobase sequence can be generated by truncation of the sequences identified above.

A probe of this invention will generally have a probing nucleobase sequence that is exactly complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., Nature Biotechnology 15:331-335 (1997)). Consequently, the probing nucleobase sequence may be only as much as 86% homologous to the probing nucleobase sequences identified above. Substantially complementary probing nucleobase sequences within the parameters described above are considered to be an embodiment of this invention.

Complements of the probing nucleobase sequence are considered to be an embodiment of this invention, since it is possible to generate a suitable probe if the target sequence to be detected has been amplified or copied to thereby generate the complement to the identified target sequence.

Detection, Identification and/or Enumeration:

By detection is meant analysis for the presence or absence of the organism optionally present in the sample. By identification is meant establishment of the identity of the organism by genus name, by genus and species name, or by other suitable category which serves to classify the organism(s) of interest. By quantitation is meant enumeration of the organisms in a sample. Some assay formats provide simultaneous detection, identification and enumeration (for example see Stender, H. et al., *J. Microbiol. Methods.* 45:31-39 (2001), others provide detection and identification (for example see Stender, H. et al., *Int. J. Tuberc. Lung Dis.* 3:830-837 (1999) and yet other assay formats just provide identification (for example see Oliveira, K et al. *J. Clin. Microbiol.* 40:247-251 (2002)).

Independent and Simultaneous Detection:

In a preferred embodiment of this invention, a multiplex assay is designed to detect one target with a labeled probe, while simultaneously detecting another target with a differently labeled probe. In a more preferred embodiment of the invention, the targets constitute rRNA or rDNA from two or more *Staphylococcus* species. In the most preferred embodiment, the assay is a PNA FISH assay designed to detect one or species of *Staphylococcus* other than aureus, and *Staphylococcus aureus*.

Antibiotic resistance

By determination of resistance to antibiotics is meant analysis of an organism's susceptibility to antibiotics based on specific genes or gene products, or mutations associated with resistance or susceptibility to antimicrobial agents.

II. Preferred Embodiments of the Invention:

a. PNA Probes:

In one embodiment, this invention is directed to PNA probes. The PNA probes of this invention are suitable for detecting, identifying and/or quantitating *Staphylococcus* species other than *S. aureus* optionally present in a sample. General characteristics (e.g., length, labels, nucleobase sequences, linkers, etc.) of PNA probes suitable for the analysis have been previously described herein. The preferred probing nucleobase sequence of PNA probes of this invention are listed in Table 1.

TABLE 1

| | 1<br>Sequence ID | 2<br>Nucleobase sequence |
|---|---|---|
| A | | |
| B | Seq. ID. No. 1 | TCT-AAC-ATG-TTC-TTT |
| C | Seq. ID. No. 2 | TCT-AGT-CTG-TTC-TTT |
| D | Seq. ID. No. 3 | TCT-AAT-ATA-TTC-CTT |
| E | Seq. ID. No. 4 | TCT-AAT-ATA-TAC-TTT |
| F | Seq. ID. No. 5 | GCT-CCA-AAT-GGT-TAC |
| G | Seq. Id. No. 6 | TCC-TCG-TCT-GTT-CGC |
| H | Seq. Id. No. 7 | CTC-CTT-ATC-TGT-TCG-C |
| I | Seq. Id. No. 8 | CTC-CTT-GTC-TGT-TCG-C |
| J | Seq. Id. No. 9 | CTT-CTC-ATC-TGT-TCG-C |
| K | Seq. Id. No. 10 | TCC-TCG-TCC-GTT-CGC |
| L | Seq. Id. No. 11 | TCC-TTG-TCC-GTT-CGC |

The PNA probes of this invention may comprise only a probing nucleobase sequence (as previously described herein) or may comprise additional moieties. Non-limiting examples of additional moieties include detectable moieties (labels), linkers, spacers, natural or non-natural amino acids, or other subunits of PNA, DNA or RNA. Additional moieties may be functional or non-functional in an assay. Generally however, additional moieties will be selected to be functional within the design of the assay in which the PNA probe is to be used. The preferred PNA probes of this invention are labeled with one or more detectable moieties selected from the group consisting of fluorophores, enzymes and haptens.

In preferred embodiments, the probes of this invention are used in in situ hybridization (ISH) and fluorescence in situ hybridization assays. Excess probe used in an ISH or FISH assay typically must be removed so that the detectable moiety of the specifically bound probe can be detected above the background signal that results from still present but unhybridized probe. Generally, the excess probe is washed away after the sample has been incubated with probe for a period of time. However, the use of self-indicating probes is a preferred embodiment of this invention, since there is no requirement that excess self-indicating probe be completely removed (washed away) from the sample since it generates little or no detectable background. In addition to ISH or FISH assays, self-indicating probes comprising the selected probing nucleobase sequence described herein are particularly useful in all kinds of homogeneous assays such as in real-time PCR or useful with self-indicating devices (e. g. lateral flow assay) or self-indicating arrays.

b. PNA Probe Sets

Probe sets of this invention comprise two or more PNAs. In one embodiment, some of the PNA probes of the set can be blocking probes. In other embodiments, the probe set can be used to analyze two of more *Staphylococcus* species other than *S. aureus*, or for the analysis of one or more *Staphylococcus* species other than *S. aureus*, and *S. aureus*.

c. Methods:

In another embodiment, this invention is directed to a method suitable for analysis of *Staphylococcus* species other than *S. aureus* optionally in a sample. The general and specific characteristics of PNA probes suitable for the analysis of *Staphylococcus* species other than *S. aureus* have been previously described herein. Preferred probing nucleobase sequences are listed in Table 1.

The method for analysis of *Staphylococcus* species other than *S. aureus* in a sample comprises contacting the sample with one or more PNA probes suitable for hybridization to a target sequence which is specific to *Staphylococcus* species other than *S. aureus*. According to the method, *Staphylococcus* species other than *S. aureus* in the sample is then detected, identified and/or quantitated or its resistance to antibiotics is determined. This is made possible by correlating hybridization, under suitable hybridization conditions or suitable in situ hybridization conditions, of the probing nucleobase sequence of a PNA probe to the target sequence of *Staphylococcus* species other than *S. aureus* sought to be detected with the presence, absence or number of the *Staphylococcus* species other than *S. aureus* organisms in the sample. Typically, this correlation is made possible by direct or indirect detection of the probe/target sequence hybrid. In a preferred embodiment, a PNA probe set is used for simultaneous analysis of *Staphylococcus* species other than *S. aureus* and *S. aureus* using differently labeled PNA probes.

Fluorescence in situ Hybridization and Real-time PCR:

The PNA probes, methods, kits and compositions of this invention are particularly useful for the rapid probe-based analysis of *Staphylococcus* species other than *S. aureus*, preferably using PNA probe sets for simultaneous analysis of two or more *Staphylococcus* species. In preferred embodiments, in situ hybridization or PCR is used as the assay format for analysis of *Staphylococcus* species other than *S. aureus*. Most preferably, fluorescence in situ hybridization (PNA FISH) or real-time PCR is the assay format (Reviewed by Stender et al. J. Microbiol. Methods 48:1-17 (2002)). Preferably, smears for PNA FISH analysis are not treated with cross-linking agents or enzymes prior to hybridization.

In one embodiment, the method includes synthesizing a nucleic acid from a sample, for example by nucleic acid amplification. Preferred nucleic acid amplification reactions are selected from the group consisting of: Polymerase Chain Reaction (PCR), Ligase Chain Reaction (LCR), Strand Displacement Amplification (SDA), Transcription-Mediated Amplification (TMA), Rolling Circle Amplification (RCA) and Q beta replicase.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.). Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/USO1/04285, which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098. For PCR methods see, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference. Nucleic acid arrays that are useful in the present invention include those that are commercially available from Affymetrix (Santa Clara, Calif.). Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA, see U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2.sup.nd Ed. Cold Spring Harbor, N.Y., 1989); Berger and Kimmel Methods in Enzymology, Vol.152, Guide to Molecular Cloning Techniques (Academic Press, Inc., San Diego, Calif., 1987); Young and Davism, P.N.A.S, 80:1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

Exemplary Assay Formats:

Exemplary methods for performing PNA FISH can be found in: Oliveira et al., J. Clin. Microbiol 40:247-251 (2002), Rigby et al., J. Clin. Microbiol. 40:2182-2186 (2002), Stender et al., J. Clin. Microbiol. 37:2760-2765 (1999), Perry-O'Keefe et al., J. Microbiol. Methods 47:281-292 (2001). According to one method, a smear of the sample, such as, but not limited to, a positive blood culture, is prepared on microscope slides and covered with one drop of the fluorescent-labeled PNA probe in hybridization buffer. A coverslip is placed on the smear to ensure even coverage, and the slide is subsequently placed on a slide warmer or incubator at 55° C. for 90 minutes. Following hybridization, the coverslip is removed by submerging the slide into a pre-warmed stringent wash solution and the slide is washed for 30 minutes. The smear is finally mounted with one drop of mounting fluid, covered with a coverslip and examined by fluorescence microscopy.

Staphylococcus species other than S. aureus optimally present in a sample which may be analyzed with the PNA probes contained in the kits of this invention can be evaluated by several instruments, such as but not limited to the following examples: microscope (for example see Oliveira et al., J. Clin. Microbiol 40:247-251 (2002)), radiation sensitive film (for example see Perry-O'Keefe et al., J. Appl. Microbiol. 90:180-189) (2001), camera and instant film (for example see Stender et al., J. Microbiol. Methods 42:245-253 (2000)), luminometer (for example see Stender et al., J. Microbiol. Methods. 46:69-75 (2001), laser scanning device (for example see Stender et al., J. Microbiol. Methods. 45:31-39 (2001) or flow cytometer (for example see Wordon et al., Appl. Environ. Microbiol. 66:284-289 (2000)). Automated slide scanners and flow cytometers are particularly useful for rapidly quantitating the number of microorganisms present in a sample of interest.

Exemplary methods for performing real-time PCR using self-reporting PNA probes can be found in: Fiandaca et al., Abstract, Nucleic Acid-Based technologies, DNA/RNA/PNA Diagnostics, Washington, DC, May 14-16, 2001, and Perry-O'Keefe et al., Abstract, International Conference on Emerging Infectious Diseases, Atlanta, 2002.

d. Kits:

In yet another embodiment, this invention is directed to kits suitable for performing an assay, which analyzes Staphylococcus species other than S. aureus optionally present in a sample. The general and preferred characteristics of PNA probes suitable for the analysis of Staphylococcus species other than S. aureus have been previously described herein. Preferred probing nucleobase sequences are listed in Table 1. Furthermore, methods suitable for using PNA probes to analyze Staphylococcus species other than S. aureus in a sample have been previously described herein.

The kits of this invention comprise one or more PNA probes and other reagents or compositions which are selected to perform an assay or otherwise simplify the performance of an assay used to analyze Staphylococcus species other than S. aureus in a sample. In preferred embodiments, the kit comprises a PNA probe set for simultaneous analysis of Staphylococcus species other than S. aureus and S. aureus using independently detectable PNA probes.

e. Exemplary Applications for Using the Invention:

The PNA probes, methods and kits of this invention are particularly useful for the analysis of Staphylococcus species other than S. aureus in clinical samples, e.g., urine, blood, wounds, sputum, laryngeal swabs, gastric lavage, bronchial washings, biopsies, aspirates, expectorates as well as in food, beverages, water, pharmaceutical products, personal care products, dairy products or environmental samples and cultures thereof. In preferred embodiments, the PNA probes are applied in a PNA probe set also containing a PNA probe for analysis of S. aureus.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLE 1

Analysis of Staphylococcus species Other Than S. aureus by Fluorescence in situ Hybridization

| PNA probe, | (Seq. ID. No.), | sequence |
|---|---|---|
| Sep16S01/tamra | (Seq. ID. No. 5) | Tamra-OO-GCT-CCA-AAT-GGT-TAC |
| Sau16S03/flu | | Flu-OO-GCT-TCT-CGT-CCG-TTC |

(Note: Conventional nomenclature used to illustrate the termini of the PNA probe; O=8-amino-3,6-dioxaoctanoic acids; flu=5(6)-carboxy-fluorescein; tamra=tetramethyl-6-carboxyrhodamine. Also note, sequence identification numbers (Seq. ID No.) are provided for internal reference, to discriminate between a core probe sequence, and an actual probe which was synthesized and used in experiments.)

Bacterial Strains

Overnight cultures of reference strains (American Type Culture Collection, (ATCC) Manassas, Va.) or clinical isolates representing Staphylococcus species other than S. aureus, including Staphylococcus epidermidis, and Staphylococcus aureus were prepared. Also, coagulase-negative staphylococci (CNS) without information about species identity were included.

Preparation of Smears.

For each strain, smears were prepared on a 8-mm diameter well of a teflon-coated microscope slide (AdvanDx, Wobum, Mass.) by mixing one drop of culture with one drop of phosphate-buffered saline containing 1% (v/v) Triton X-100. The slide was then placed on a 55° C. slide warmer for 20 min at which point the smears were dry. Subsequently, the smears were disinfected by immersion into 96% (v/v) ethanol for 5-10 minutes and air-dried.

Fluorescence in situ Hybridization (FISH).

Smears were covered with a drop of hybridization solution containing 10% (w/v) dextran sulfate, 10 mM NaCl, 30% (v/v) formamide, 0.1% (w/v) sodium pyrophosphate, 0.2% (w/v) polyvinylpyrrolidone, 0.2% (w/v) ficoll, 5 mM Na2EDTA, 1% (v/v) Triton X-100, 50 mM Tris/HCl pH 7.5 and 500 nM. Sep16S01/tamra and/or Sta16S03/flu. Coverslips were placed on the smears to ensure even coverage with hybridization solution, and the slides were subsequently placed on a slide warmer (Slidemoat, Boekel, Feasterville, Pa.) and incubated for 90 min at 55° C. Following hybridization, the coverslips were removed by submerging the slides into approximately 20 ml/slide pre-warmed 25 mM Tris, pH 10, 137 mM NaCl, 3 mM KCl in a water bath at 55° C. and washed for 30 min. Each smear was finally mounted using one drop of Mounting medium (AdvanDx, Woburn, Mass.) and covered with a coverslip. Microscopic examination was conducted using a fluorescence microscope equipped with a FITC/Texas Red dual band filter set. *Staphylococcus* species other than *S. aureus* was identified by red fluorescent cocci and *Staphylococcus aureus* was identified as green fluorescent cocci.

EXAMPLE 2

Evaluation of PNA Probe for Analysis of *Staphylococcus* species Other Than *S. aureus*

This experiment was designed to test the performance of the PNA probes of this invention for analysis of *Staphylococcus* species other than *S. aureus* by fluorescence in situ hybridization. Methods and probe mixtures are as described in Example 1, with the exception that PNA probe, Sta16S03 was not added.

TABLE 2

| 1<br>A Species | 2<br>Source | 3<br>Sep16S01/tamra |
|---|---|---|
| B *Staphylococcus aureus* | Clinical isolate | Negative |
| C *Staphylococcus epidermidis* | Clinical isolate | Red |
| D CNS | Blood culture bottle | Red |
| E CNS | Blood culture bottle | Red |

With reference to Table 2, the table displays the data from Example 2, with species identification in column 1, source of the culture in column 2, and signal from the tamra-labeled probe, Sep16S01, in column 3. With reference to Table 2, column 3, row C, the red fluorescent signal indicates that Sep16S01 hybridizes to *S. epidermidis*, the most commonly occurring coagulase-negative *Staphylococcus* species, and to non-identified coagulase-negative staphylococci (rows D, E), but not to *S. aureus* (row B). Sep16S01 is therefore suitable for analysis of *Staphylococcus* species other than *S. aureus*.

EXAMPLE 3

Evaluation of a PNA Probe set for Analysis of *Staphylococcus* species other than *S. aureus*, and *S. aureus*

This experiment was designed to test the performance of the PNA probe set of this invention comprising the PNA probe for analysis of a mixture of *Staphylococcus* species other than *S. aureus* together with a PNA probe for analysis of *S. aureus*. The two probes were labeled with tamra (red) and fluorescein (green), respectively, which can be view simultaneously using the FITC/Texas Red dual band filter. Methods and probe mixtures are as described in Example 1 with the exception that a clinical isolate of Enterococcus faecalis was included as a representative non-staphylococci.

TABLE 3

| 1<br>A Species | 2<br>Source | 3<br>Sta16S03/flu<br>Sep16S01/tamra |
|---|---|---|
| B *Staphylococcus aureus* | Clinical isolate | Green |
| C *Staphylococcus epidermidis* | Clinical isolate | Red |
| D *Enterococcus faecalis* | Clinical isolate | Negative |
| E *Staphylococcus aureus* | Blood culture bottle | Green |
| F CNS | Blood culture bottle | Red |
| G CNS | Blood culture bottle | Red |

With reference to Table 3, the table displays the data from Example 3, with species identification in column 1, source of the culture in column 2, and signal from the tamra-labeled probe, Sep16S01, or flu-labeled probe Sta16S03 in column 3. With reference to Table 3, column 3, row B, the fluorescent signal seen in the presence of *S. aureus* cells is green, indicating hybridization of the Sta16S03 probe. In the same column, row C, the fluorescent signal is red, in the presence of *S. epidermidis* cells, indicating hybridization of the Sep16S03 probe. The absence of fluorescent signal in row D indicates that neither the Sta16S03 nor the Sep16S01 probes hybridize to *Enterococcus faecalis* cells. *Enterococcus faecalis* is a Gram-positive cocci which has a similar appearance to staphylococci by bright field microscopy and could be potentially confused with staphylococci. The data also demonstrates that the same result can be obtained for *S. aureus* cells regardless of the source of the sample (Clinical isolate, row B, or Blood culture bottle, row E). The results show that the PNA probe set is suitable for simultaneous analysis of *S. aureus* and *Staphylococcus* species other than *S. aureus*.

EXAMPLE 4

Analysis of Mixed Cultures of *Staphylococcus* species Other Than *S. aureus* and *S. aureus*.

This experiment was designed to show the advantage of using a probe set comprising the PNA probe of this invention for analysis of a mixture of *Staphylococcus* species other than *S. aureus* together with a PNA probe for analysis of *S. aureus*. The two probes were labeled with tamra (red) and fluorescein (green), respectively, which can be view simultaneously using the FITC/Texas Red dual band filter. Methods and probe mixtures are as described in Example 1 with the exception that in part of the experiment the Sep16S01 probe was not used.

TABLE 4

| 1<br>A Species | 2<br>Source | 3<br>Sep16S01/tamra<br>Sta16S03/flu | 4<br>Sta16S03/flu |
|---|---|---|---|
| B *S. aureus*/CNS | Clinical isolates[1] | Red/Green | Green |
| C *S. aureus*/CNS | Blood culture bottle[2] | Red/Green | Green |

[1]The smears were prepared by mixing the pure isolates.
[2]The smears were prepared directly from GPCC-positive blood culture bottle.

With reference to Table 4, the table displays the data from Example 4, with species identification in column 1, source of the culture in column 2, signal from the tamra-labeled probe, Sep16S01, or flu-labeled probe Sta16S03 in column 3, and signal from the Sta16S03 probe only in column 4. As can be seen in Table 4, column 3, when using the probe set of Sep16S01 and Sta16S03 both green and red fluorescent cocci were present in the same fields of view when detecting a mixed culture of *S. aureus* and CNS. The source of the sample did not effect the result, as can bee seen by comparing rows B and C of Table 2. In contrast, only green fluorescent cocci where observed when using Sta16S03 alone hereby missing the presence of CNS (see Table 4, column 4).

EXAMPLE 5

Analysis of *Staphylococcus* species Other Than *S. aureus* by Fluorescence in situ Hybridization.

| PNA probe, | (Seq. ID. No.), | sequence |
|---|---|---|
| CNS3 | (Seq. ID. No. 6) | Tamra-OO-TCC-TCG-TCT-GTT-CGC |
| CNS4 | (Seq. ID. No. 7) | Tamra-OO-CTC-CTT-ATC-TGT-TCG-C |
| CNS5 | (Seq. ID. No. 8) | Tamra-OO-CTC-CTT-GTC-TGT-TCG-C |

This experiment was designed to test PNA probes directed against *Staphylococcus* species other than *S. aureus*. Methods and probe mixtures are as described in Example 1 with the exception that the PNA probe mixture consisted of 500 nM of either of the tamra labeled PNA probes described above, CNS3, CNS4, or CNS5. All the probes in this experiment are directed towards a phylogenetically conserved region of rRNA target sequence which varies slightly between *Staphylococcus* species. Also different from Example 1, non-identified CNS cells were omitted and overnight cultures of ATCC reference strains of *Staphylococcus hominis, Staphylococcus haemolyticus, Staphylococcus lugdunensis,* and *Staphylococcus saprophyticus*, were included.

TABLE 5

| | 1<br>Species | 2<br>CNS3 | 3<br>CNS4 | 4<br>CNS5 |
|---|---|---|---|---|
| A | | | | |
| B | *Staphylococcus aureus* | Negative | Negative | Negative |
| C | *Staphylococcus epidermidis* | Red | Negative | Red |
| D | *Staphylococcus hominis* | Red | Negative | Red |
| E | *Staphylococcus haemolyticus* | Red | Red | Red |
| F | *Staphylococcus lugdunensis* | Negative | Red | Red |
| G | *Staphylococcus saprophyticus* | Negative | Red | Red |

With reference to Table 5, the table displays the data from Example 5, with species identification in column 1, fluorescent signal for CNS3 probe in column 2, CNS4 probe in column 3, and CNS5 probe in column 4. With reference to row B, columns 2, 3 and 4, none of the probes tested result in a red fluorescent signal in *S.aureus*. By contrast, all of the species described in rows C through G display red fluorescence in two or more cases when detected with the probes described in columns 2, 3 and 4. These results show that probes CNS3, CNS4, and CNS5 can all be used individually for detection of some *Staphylococcus* species other than *S.aureus*.

EXAMPLE 6

Analysis of *Staphylococcus* species Other Than *S. aureus* by Fluorescence in situ Hybridization.

This experiment was designed to test PNA probe mixtures directed against a cohort of *Staphylococcus* species other than *S. aureus* together with a PNA probe for analysis of *S. aureus*. Methods and probe mixtures are as described in Example 1 with the exception that the PNA probe mixture consisted of 500 nM of Sta16S03 (Set A), or 500 mM Sta16S03 plus 500 nM of each of the three tamra labeled PNA probes described in Example 5, CNS3, CNS4, and CNS5 (Set B). All the probes in this experiment are direct towards a phylogenetically conserved region of rRNA target sequence which varies slightly between *Staphylococcus* species. Also different from Example 1, non-identified CNS cells were omitted and overnight cultures of ATCC reference strains of *Staphylococcus hominis, Staphylococcus haemolyticus, Staphylococcus lugdunensis, Staphylococcus saprophyticus, Staphylococcus schleiferi,* and *Enterococcus faecalis* were included.

TABLE 6

| | 1<br>Species | 2<br>Signal Set A | 3<br>Signal Set B |
|---|---|---|---|
| A | | | |
| B | *Staphylococcus aureus* | Green | Green |
| C | *Staphylococcus epidermidis* | Negative | Red |
| D | *Staphylococcus hominis* | Negative | Red |
| E | *Staphylococcus haemolyticus* | Negative | Red |
| F | *Staphylococcus lugdunensis* | Negative | Red |
| G | *Staphylococcus saprophyticus* | Negative | Red |
| H | *Staphylococcus schleiferi* | Green | Red |
| I | *Enterococcus faecelis* | Negative | Negative |

With reference to Table 6, the table displays the data from Example 6, with species identification in column 1, fluorescent signal for Set A probe mixture in column 2, and the fluorescent signal for Set B probe mixture in column 3. With reference to column 2, use of probe Set A results in green fluorescent signal in two of the bacterial species tested, *S. aureus*, and *S. scheiferi*, and no fluorescent signal in the other bacteria tested. As can be seen in column 3, use of probe Set B resulted in green fluorescent signal for *S.aureus*, and red fluorescent signal for *S. epidermidis, S. hominis, S. haemolyticus, S. lugdunensis, S. saprophyticus,* and *S. scheiferi*. No fluorescent signal was observed for *Enterococcus faecalis* with either probe set.

It has been demonstrated in previous experiments that the Sta16S03 probe forms a stabile hybrid with *S.schleiferi* even though the probe and target sequence are not perfectly complementary (Oliveira et al., J. Clin. Microbiol. 40:247-251 (2002)). The change seen in the fluorescence of *S. schleiferi* from green with probe Set A to red with probe Set B reflects the competition between the probes for the target sequence. Since all probes are directed to similar target sequences, yet only one probe at a time can be bound to a target sequence, the most stabile hybrid is formed. It this way cross hybridization of the Sta16S03 probe to *S.schleiferi* is prevented by inclusion of the other probes in Set B.

These data demonstrate that a probe mixture can be made which detects a cohort of species by one fluorescent label, and a single species with a second fluorescent label. Though the *Staphylococcus* species tested in this experiment are considered to be the most clinically relevant, other experiments not included here demonstrated that many other *Staphylococcus* species can be detected with probe Set B. Of all species tested with probe Set B, only *S. aureus* resulted in a green fluorescent signal.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

A number of embodiments of the invention have been described. Nevertheless, it will be understood that various modifications may be made without departing from the spirit and scope of the invention. Accordingly, other embodiments are within the scope of the following claims.

We claim:

1. A PNA probe set consisting of SEQ ID NO:6, SEQ ID NO:7 and SEQ ID NO:8.

2. The PNA probe set of claim 1, wherein the probes are differently labeled for independent analysis of two or more *Staphylococcus* species.

3. A kit suitable for performing an assay for analysis of one or more *Staphylococcus* species other than *S. aureus* in a sample, wherein said kit comprises:
   a) a PNA probe set according to claim 1 and b) other reagents or compositions necessary to perform the assay.

4. A PNA probe set consisting of three PNA probes SEQ ID NO 6, SEQ ID NO: 7 and SEQ ID NO: 8, wherein the PNA probe comprising SEQ ID NO: 6 is 15 nucleobases in length, wherein the PNA probe comprising SEQ ID NO: 7 is 16 nucleobases in length and wherein the PNA probe comprising SEQ ID NO: 8 is 16 nucleobases in length.

5. A PNA probe set consisting of SEQ ID NO:6, SEQ ID NO:7 and SEQ ID NO:8 and at least one PNA blocking probe for the analysis of one or more *Staphylococcus* species other than *S. aureus*.

6. A PNA probe set consisting of SEQ ID NO:6, SEQ ID NO:7 and SEQ ID NO:8 and at least one PNA probe for the analysis of *S. aureus*.

* * * * *